United States Patent [19]

Zhan

[11] Patent Number: 6,007,822
[45] Date of Patent: Dec. 28, 1999

[54] ANIMAL FEED COMPOSITIONS AND USES OF TRITERPENOID SAPONIN OBTAINED FROM CAMELLIA L. PLANTS

[75] Inventor: Yong Zhan, Hangzhou, China

[73] Assignee: Zhejian Agricultural University, Zhejiang, China

[21] Appl. No.: 08/930,754

[22] PCT Filed: Aug. 16, 1996

[86] PCT No.: PCT/CN96/00070

§ 371 Date: Jan. 22, 1998

§ 102(e) Date: Jan. 22, 1998

[87] PCT Pub. No.: WO97/29630

PCT Pub. Date: Aug. 21, 1997

[30] Foreign Application Priority Data

Feb. 14, 1996 [CN] China .................................. 96101151
May 17, 1996 [CN] China .................................. 96105034

[51] Int. Cl.⁶ .................................................. A61K 35/78
[52] U.S. Cl. ...................... 424/195.1; 426/635; 514/783; 514/25; 536/4.1
[58] Field of Search ........................ 424/195.1; 426/635; 514/783, 25; 536/4.1

[56] References Cited

U.S. PATENT DOCUMENTS 4,536,494  8/1985  Carter .
4,820,739  4/1989  Ramallo et al. ........................ 514/763

FOREIGN PATENT DOCUMENTS 86106634   9/1987   China .
 1054788   9/1991   China .
61-007290  1/1986   Japan .
 61-7290   1/1986   Japan .
62-282553  12/1987  Japan .
07075506   3/1995   Japan .
08131089   5/1996   Japan .
09248135   9/1997   Japan .

OTHER PUBLICATIONS

Jin et al. *Tiaran Chanwu Yanjiu Yu Kaifa*, vol. 5(2): 48–52, 1993.
Itowaka et al. *Yakugaku Zasshi*, vol. 88(11): 1463–1466, 1968.
Kurokawa et al. *Antiviral Research*, vol. 22(2/3) : 175–188, 1993.
May et al. *Arzneim–Forsch.*, vol. 28(1): 1–7, 1978.
Hamilton–Miller, J. M. T. *Antimicrob. Agents Chemother.*, vol. 39(11) : 2375–2377, 1995.
Nagata et al. *Agric. Biol. Chem.*, vol. 49(4): 1181–1186, 1985.
Yo Shioka et al. *Chem. Pharm. Bull.*, vol. 20(6): 1237–1242, 1972.
Sekine et al. *Chem. Pharm. Bull.*, vol. 41 (6): 1185–1187, 1993.
Hamaya et al. *Nippon Shokubutsu Byori Gakkaiho*, vol. 50(5) pp. 628–636, 1984.
Shcheglov et al. *Antibiotiki*, vol. 24 : 270–273, 1979.

*Primary Examiner*—Howard C. Lee
*Attorney, Agent, or Firm*—Harness, Dickey & Pierce, P.L.C.

[57] ABSTRACT

An animal feed composition is disclosed which comprises triterpenoid saponin obtained from Camellia L. plants and having the properties of improving immune function, enhancing antibacterium and antivirus activities, antimutation, antioxidation and scavenging free radicals in human beings and animals.

10 Claims, No Drawings

ANIMAL FEED COMPOSITIONS AND USES OF TRITERPENOID SAPONIN OBTAINED FROM CAMELLIA L. PLANTS

This application is a 371 of PCT/CN96/00070 filed on Aug. 16, 1996.

TECHNICAL FIELD

The present invention relates to a method of preventing animal diseases and promoting animal growth and development. In particular, the method of the present invention comprises extracting bioactive ingredients from oil plants and adding them into feed and food as a feed additive and nutrient, respectively, to improve the immune function of animals and to promote the growth and developement of animals.

BACKGROUND ART

Plants belonging to Camellia L. are very popular in China, Japan, India and many other South-East Asian countries. Among of them, plants from three species C. sinensis, C. oleifera and C. japonica, are of significant economic value. For example, leaves of C. sinensis plants can be used to produce tea and seeds of C. oleifera plants can be used to produce edible oil, while C. japonica plants are useful as ornamental plants.

With the development of the modern feed industry, a number of antibiotics have been used as feed additive to prevent animal diseases and to promote animal growth. In 1990, while about 2000 tons of antibiotics were used as feed additives in China, about 1350 tons and 1300 tons of antibiotics were used in West Europe and Japan, respectively, in poultry and livestock feed. Recently, sale value of antibiotics reached US $1.019 billions in the USA and utilization of antibiotics is increasing by 3% annually world wide. Long-term utilization of antibiotics, however, can result in drug-resistance of microbes which will create world-wide environment pollution via R-factor translocation, and residual problem in animal products which will be a that to human health. The WHO (World Health Organization) and the FAO (Food and Agriculture Organization, United Nations) are taking great consideration about research on alternatives of antibiotics as feed additives. Currently, research and development on natural material as a feed additive has made a great deal of progress. For example, feed microbes and traditional Chinese medicines have been used extensively. However, feed microbes are prone to becoming inactive during feed processing and can only replace antibiotics partially. Traditional Chinese medicine additives can not be used extensively, due to their sophistication in composition and instability in function. Therefore, there is a necessity to (1) use natural bioactive ingredients as feed additive to replace antibiotics, (2) exclude the residue of antibiotics residue in animal products, (3) improve product quality, and (4) alleviate environmental pollution.

S. Aoyama first separated thea saponin from tea seed cake in 1931. (Journal of Pharmacology, 51(5): 367, 1931). However he did not obtained this pure chemical. In 1952, M. Ishidate and Y. Ueda of Tokyo University obtained the pure crystals of thea saponin. (Ishidate, M. and Ueda, Y., Journal of Pharmacology, 72 (11): 1525, 1952.). From the 1970's, a series of studies on separation, characterization and utilization of thea saponin were conducted in major tea-producing countries. Many extracting methods and products had been developed during this period.

It is now clear that saponin obtained from Camellia L. belongs to triterpenoid compounds. It is a group of complicated compounds composed of aglycone ($C_{30}H_{50}O_6$), sugars and organic acids. The chemical structures of saponin obtained from Camellia L. have been disclosed in many references. For example, in I. Yoshioka et al., Chemical Pharmacology Bulletin (Tokyo) 1970, 18. 1610; Yoshioka, et al., Thea sapogenol A., The Major Sapogenol of the Seeds Saponin of Thea"; Sinensis L., Tetrahedron Letters, 1966 (48): 5979–5984, 5973–5978; and I. Yoshioka, et al., Saponin and Sapogenol III Seeds Sapogenols of Thea Sinensis L (3), Thea Sapogenol E and Minor Sapogenols, Chem. Phar. Bull. 1971, 19 (6) 1186–1199.

Development in thea saponin research offers great opportunity for complete utilization of by-products of tea seed and tea leaves. In 1972, G. R. Roberts and his colleague (G. R. Roberts et al., Tea QUARTERLY 43 (3), 1972) from Sri Lanka improved thea saponin extracting technology, industrialized its preparation, and suggested several other methods to use tea seed cake from Camellia plants, (R. L. Wickremastinghe et al., 1972. Tea Quarterly 43 (3)). As estimated by T. Yaziciglu and his colleague, about 600 tons of thea saponin could be extracted from 15,000 tons of tea seed in Turkey. So far, industrialization of thea saponin production has been possible, and Nippon Isome Grease Chemical Co. is already commercializing the production of thea saponin.

Saponin obtained from Camellia L. has extensive utilization in industry. Its utilization in medicine was the earliest research field. However, this field developed slowly though there are many pharmacologists investigating the problem. Pharmacological effects of the saponin include antiosmosis, antiphlogistics, and control of coughing. It was reported that the saponin has special effect on many kinds of oedema (dropsy).

Industry utilization of saponin obtained from Camellia L. is a newly developed field. It could be used to produce kinds of water and oil emulsion, preservatives, foaming agent in the beer industry and detergents in daily industry. It could maintain the color of fabrics as it resists damage to dye on the fabrics. When used in laundering process, it prevents shrinking of woolen products and maintains the luster of fabrics as well. The saponin can also be used in photographic industry.

Saponin obtained from Camellia has extensive usage in agriculture, expecially as insecticide, germicide and binding agent in spray pesticide. Its major benefit is to avoid pesticide residue and protect environment.

However, research on the utilization of saponin obtained from Camellia as feed additive to replace antibiotics has not been documented yet, nor have the effects of said saponin on animal growth and immune function promotion.

After research and development of saponin obtained from Camellia L. for many years, the present inventor has unexpectedly found that saponins extracted from the seed cake of Camellia L. could improve immune function and has the added beneficial effects of being anti-bacterial and anti-viral. It is, in fact, safe for animal consumption under some conditions and can enhance the growth of the animals.

It is one object of the present invention to provide a method of promoting the growth of animals.

It is another object of the present invention to provide a method of improving immune function and anti-bacterial and anti-viral effects.

It is another object of the present invention to provide a use of the bioactive extract of oil plants as feed additive.

It is another object of the present invention to provide a novel health care agent.

DETAILED DESCRIPTION OF THE INVENTION

As used in the context of the present invention, the term "seed cake" refers to residues obtained from seeds of oil-bearing plants after the extraction of oil therefrom.

The term "Camellia seed cake" refers to seed cake obtained from Camellia L. plants, such as from *C. sinensis, C. oleifera* and *C. japonica* plants.

Triterpenoid saponin used in this invention was extracted from oil plants. Preferably, it is obtained from plants belonging to the camellia family, and most preferably is obtained from leaves and seeds of Camellia plants.

The process used in the present invention for the production of triterpenoid saponin is described as follows.

Seed cake remaining after oil extraction is grounded, then soaked in alcohol and other organic reagents. The organic extract is filtered, condensed and dried to obtain triterpenoid saponin powder. Temperature ranges from 20 to 50° C., and preferably from 30 to 40° C. Concentration of the organic range rangents from 60 to 90%. The drying method can be vacunm-drying or sprap-drying.

Saponin obtained according to this invention can be used directly as feed additive or health care agent. It can also be used in combination with trace elements.

Dosage and application methods of this saponin preparation are similar to those used for conventional feed additives and health care agents. Its content in feed can be in the range of 50–1500 ppm, and is preferably in the range of 250–750 ppm.

This invention offers a bioactive ingredient from natural Camellia seed cake to be used as a feed additive. It can replace antibiotics in conventional feed completely (thus avoiding antibiotic residues in animal products), produce high-quality animal products, reduce environment pollution and increase animal production performances. It can also be used as a nutritive health care agent. Therefore, low valued oil-seed meal can be used effectively and have a better social and economic benefit.

The following examples are used to illustrate the invention in more detail, but they are not intended to limit the scope of the present invention in any way.

EXAMPLE 1

Preparation of bioactive feed additive A

Eight thousand grams of Camellia olefera seed cake were extracted three times with 83 percent alcohol (v/v). All the organic extracts were combined and vacuum-dried. Eight Hundred grams of extracted powder were obtained, which was used directly as a feed additive.

EXAMPLE 2

Preparation of bioactive feed additive B

Twenty five grams of zinc sulfate of feed grade and 25 grams of manganese sulfate of feed grade were added to 1000 grams of the feed additive A obtained in Example 1. After mixing evenly, feed additive B was then obtained.

EXAMPLE 3

Preparation of bioactive feed additive C

One Hundred grams of zinc sulfate of feed grade, 100 grams of manganese sulfate of feed grade and 50 grams of vitamin C were added to 1000 grams of the above mentioned additive A. After mixing evenly, feed additive C was then obtained.

EXAMPLE 4

Improvement of survival rate of livestock

From July 1992 to June, 1994, 3108 one-day old chicken (4 batches), 320 eleven-day old piglets (8 batches) and 600 growing chicken for egg purpose were allocated into control and test groups to determine survival rates. Feed used in control groups were AMV broiler complete feed, PCS pig complete feed and Wanghai brand complete feed for chicken layers. The formulations of the three feed compositions were as follows:

| Formulation of PCS Complete Feed for Pig | | |
|---|---|---|
| Ingredients | piglet period | growing period |
| corn (%) | 51.7 | 48.2 |
| wheat bran (%) | 16.00 | 15.0 |
| middlings (%) | 10.0 | 20.0 |
| fish meal (%) | 6.0 | 4.0 |
| limestone (%) | 1.0 | 1.0 |
| $CaHPO_3$ (%) | 0.5 | 0.5 |
| NaCl (%) | 0.3 | 0.3 |
| additives (%) | 1.0 | 1.0 |
| Olaquindox (ppm) | 80.0 | 60.0 |

| AMV Complete feed for broiler | | |
|---|---|---|
| Ingredients | 0–21 days | 22–49 days |
| corn (%) | 57 | 67 |
| soybean meal (%) | 30 | 23 |
| middilings (%) | 5 | — |
| concentrate 1 (%) | 5 | — |
| concentrate 2 (%) | — | 5 |
| fishmeal (%) | 3.0 | 2.0 |
| yeast (%) | — | 3.0 |
| colistin sulfate (ppm) | 6.0 | 6.0 |
| bacitracin zinc (ppm) | 30.0 | 30.0 |
| coccidiostatics (ppm) | — | 125 (22-42 days) |

| Wanghai brand feed for growing layers | |
|---|---|
| corn % | 60 |
| wheat bran (%) | 10.0 |
| soybean meal (%) | 17.0 |
| fishmeal (%) | 9.0 |
| bone meal (%) | 2.0 |
| additive (%) | 2.0 |
| terramycin (ppm) | 100 |

In test groups, 500 ppm of bioactive additive obtained from practical Example 1 was used to replace all the antibiotics in the control diets. The survival rates after 49, 120 and 21 days of experiments were estimated for broilers, piglets and growing layers respectively. The results are listed in Table 1.

TABLE 1

Survival rates of livestock

| | broiler | | growing layers | | piglet | |
|---|---|---|---|---|---|---|
| group | tested | survival rate (%) | tested | survival rate (%) | tested | survival rate(%) |
| saponin | 1845 | 95.30 | 300 | 88.00** | 160 | 100.00 |
| antibiotics | 1263 | 94.4 | 300 | 77.00 | 160 | 98.13 |

**$P < 0.01$

Results indicated that Sasanqua saponin could be used to replace antibiotics in the diets. The survival rates were increased by 0.95%, 14.29% ($P<0.01$) and 1.91% respectively for broilers, growing layers and piglets.

EXAMPLE 5

Effect of increasing live weight gain of livestock

Under the same experimental designs as in example 4, the effects of the bioactive agents obtained by this invention on body weight gain were tested at day 49 (Table 2). The results were showed in table 2 below.

TABLE 2

Body weight gain of livestock

| group | broiler | | | piglet | | |
|---|---|---|---|---|---|---|
| | tested | net gain (g/each) | ADG (g/day) | tested | net gain (kg/each) | ADG (g/day) |
| saponin | 1845 | 2019.8 | 41.2 | 160 | 25.17 | 508.27 |
| antibiotics | 1263 | 1971.2 | 40.2 | 160 | 22.92 | 463.60 |

In broilers, net gain increased by 48.6 grams/bird and ADG increased by 2.49%. In piglet, net gain increased by 2.25 kg/animal and ADG increased by 9.64%.

EXAMPLE 6

Effect of increasing feed efficiency

Under the same experimental conditions as described in Example 4, the effects of the feed additive of the present invention on feed efficiency were tested. The results were showed in Table 3.

TABLE 3

Feed efficiency

| group | broiler | | piglet | |
|---|---|---|---|---|
| | tested | feed:gain | tested | feed:gain |
| saponin | 1845 | 2.06:1** | 160 | 2.42:1 |
| antibiotics | 1263 | 2.26:1 | 160 | 2.54:1 |

**: p < 0.05

Results suggest that replacement of antibiotics with bioactive saponin decreased ratio of feed-to-gain by 9.71% (P<0.05) and 4.72% respectively for broilers and piglets.

EXAMPLE 7

Effect of improving meat nutrient contents

Under the same experimental design as in Example 4, fat and amino acid profiles in chicken at day 49 were determined. Results suggest that saponin could improve chicken nutrient quality, especially threonine content by 8.38% (P<0.05).

EXAMPLE 8

Effect of improving processing value of livestock products

Under the same experimental design as in Example 4, some processing indices at day 49 were tested. Saponin replacement increased dressing percentage and total meat pigment by 1.93% and 7.48% respectively in broilers. Meat water loss percentage and pH decreased by 1.37% and 2.50% respectively. Results indicate that saponin addition is beneficial to meat processing and storage.

EXAMPLE 9

Effect of reducing heavy metals in meat

Under the same experimental design as in Example 4, contents of heavy metal elements in meat were determined with an atomic absorption spectrometer at day 49. Results indicated that saponin reduced Cd and Pb contents in meat by 94.41 and 38.28% in broilers.

EXAMPLE 10

Effect of antioxidation

To conventional feed, 750 ppm bioactive agent obtained in Example 1 was added. After incubation for 49 days at 40° C., acidity of the feed was determined by KOH titration method, peroxidation value was determined by sodium thiosulfate method, and the content of Vitamin A was determined by HPLC. Results suggested that acidity and peroxidation value were reduced by 38.79% and 21.28% (P<0.05) respectively, and saponin had protection over fat and Vitamin A.

EXAMPLE 11

Effect of increasing immune function and antiviruses

Saponin obtained from Example 1 was added into broiler feed at a dosage of 750 ppm. After IBD viruses were injected into chickens. at day 28, blood and spleen samples were taken at day 34. As a result, immunoglobin; T lymphocytes transformation rate, interleukin 2(IL-2) and erythrocyte C3b receptors were increased by 11.56% (P<0.01), 54.09% (P<0.05), 52.66% (P<0.05) and 21.71% (P<0.05) respectively. This suggests that saponin could improve immune function and has an anti-viral effect.

EXAMPLE 12

Effect of free radical scavenge and antimutation

Light emision analysis results showed that saponin obtained from Example 1 cleared about 94.40% of superoxide anion radical ($O_2^-$) (P<0.01) and 78.19%(P<0.01) hydroxyl radical ($OH^-$). In adult cocks and hens, ethyl methanesulfonate (EMS) was used at the dosage of 82 mg/kg and 80 mg/kg respectively via intramuscular injection for three days. Sasanqua saponin addition at 750 ppm decreased cock sperm deformation rate by 58.96% (P<0.01), increased hen ovulation rate by 28.64%, and increased egg fertility by 75.54 (P<0.01). These results suggested that the extracted bioactive additive was effective in protecting cells against deformation induced by alkylating agents.

EXAMPLE 13

Effect of anti-bacteria

Seven hundred fifty ppm extracted bioactive agent was added into a culture dish to evaluate its antibacterial effect. Results indicate that suppressing concentrations for *E. Coli* and salmonella were 1.25–0.5 mg/mL and 0.1563–0.0390 mg/mL respectively.

EXAMPLE 14

Effect of increasing hormone, protein and enzyme levels

Under the same experimental design as in Example 4, venous blood samples were taken at day 49. Results showed that saponin addition increased serum testosterone level by 25.61% (P<0.05), serum total protein content by 11.08%, alkaline phosphatase activity by 19.023%, amylase activity by 16.79% and total proteolytic enzyme activity by 49.37%.

EXAMPLE 15

Effect on growth of aquatics

Addition of 10 ppm Sasanqua saponin in turtle, prawn and eel diets improved their survival rates and growth rates.

EXAMPLE 16

Safety test of Sasanquasaponin

Tea saponin obtained from Example 1 was added at 5000 ppm in the diet of rats. After 30 days of feeding, no abnormal signs were observed in rat somatic cells and reproductive cells. Test results indicated that tea saponin is safe as a feed additive.

It will be appreciated that it is not intended to limit the invention to the above examples only, many variations thereto and modifications thereof being possible to one skilled in the art without departing from its scope, which is defined by the appended claims.

What we claimed is:

1. An animal feed composition comprising:
   (a) an animal feed; and
   (b) triterpenoid saponin obtained from Camellia L. plants.
2. The composition according to claim 1, wherein the content of component (b) is about 50–1500 ppm by weight of feed.
3. The composition according to claim 2, wherein the content of component (b) is about 250–750 ppm by weight of feed.
4. The composition according to claim 1, wherein the animal being fed includes livestock and poultry.
5. The composition according to claim 4, wherein the livestock and poultry include chickens, ducks or pigs.
6. The composition according to claim 1, wherein said Camellia L. plants are selected from the group consisting of C. sinensis, C. oleifera and C. japonica.
7. The composition according to claim 6, wherein said triterpenoid saponin is obtained from the seeds or leaves of said plants.
8. The composition according to claim 7, wherein said triterpenoid saponin is extracted from Camellia seed cake with an organic solvent at room temperature.
9. A method of using of triterpenoid saponin as a bioactive agent for improving immune function and for enhancing antibacterium and antivirus activities in human beings and animals, the method comprising the step of administrating to human beings or animals a composition comprising triterpenoid saponin obtained from Camellia L. plants.
10. A method of using triterpenoid saponin as a bioactive agent for enhancing animal performance and for improving meat quality, the method comprising the step of feeding animals with animal feed composition comprising an animal feed and triterpenoid saponin obtained from Camellia L. plants.

* * * * *